United States Patent
Santos et al.

(10) Patent No.: US 12,363,488 B2
(45) Date of Patent: *Jul. 15, 2025

(54) ELECTRONIC DEVICE USING A COMPOUND METRIC FOR SOUND ENHANCEMENT

(71) Applicant: STARKEY LABORATORIES, INC., Eden Prairie, MN (US)

(72) Inventors: Joao Felipe Santos, Montreal (CA); Tao Zhang, Eden Prairie, MN (US); Yan Zhao, Columbus, OH (US); Buye Xu, Eden Prairie, MN (US); Ritwik Giri, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/367,017

(22) Filed: Sep. 12, 2023

(65) Prior Publication Data

US 2023/0421973 A1 Dec. 28, 2023

Related U.S. Application Data

(63) Continuation of application No. 17/834,288, filed on Jun. 7, 2022, now Pat. No. 11,812,223, which is a (Continued)

(51) Int. Cl.
*H04R 25/00* (2006.01)
*G10L 15/16* (2006.01)
(Continued)

(52) U.S. Cl.
CPC .............. *H04R 25/50* (2013.01); *G10L 15/16* (2013.01); *G10L 21/0208* (2013.01); (Continued)

(58) Field of Classification Search
CPC . A61N 1/36039; G10L 15/16; G10L 21/0208; G10L 25/30; G10L 25/48;
(Continued)

(56) References Cited

U.S. PATENT DOCUMENTS 9,633,671 B2 4/2017 Giacobello et al.
10,812,915 B2 * 10/2020 Santos ................... G10L 25/84
(Continued)

FOREIGN PATENT DOCUMENTS

EP 3229496 10/2017

OTHER PUBLICATIONS

Clevert et al., "Fast and accurate deep network learning by exponential linear units (ELUs)," arXiv preprint arXiv:1511.07289, 2015.
(Continued)

*Primary Examiner* — Phylesha Dabney
(74) *Attorney, Agent, or Firm* — Mueting Raasch Group

(57) ABSTRACT

A method, comprising receiving at least one sound at an electronic device. The at least one sound is enhanced for the at least one user based on a compound metric. The compound metric is calculated using at least two sound metrics selected from an engineering metric, a perceptual metric, and a physiological metric. The engineering metric comprises a difference between an output signal and a desired signal. At least one of the perceptual metric and the physiological metric is based at least in part on input sensed from the at least one user in response to the received at least one sound.

23 Claims, 7 Drawing Sheets

Related U.S. Application Data continuation of application No. 17/074,144, filed on Oct. 19, 2020, now Pat. No. 11,363,390, which is a continuation of application No. 16/170,858, filed on Oct. 25, 2018, now Pat. No. 10,812,915.

(60) Provisional application No. 62/577,903, filed on Oct. 27, 2017.

(51) Int. Cl.
*G10L 21/0208* (2013.01)
*G10L 25/30* (2013.01)
*G10L 25/48* (2013.01)
*G10L 25/84* (2013.01)
*A61N 1/36* (2006.01)

(52) U.S. Cl.
CPC .............. *G10L 25/30* (2013.01); *G10L 25/48* (2013.01); *G10L 25/84* (2013.01); *H04R 25/507* (2013.01); *A61N 1/36039* (2017.08); *H04R 25/407* (2013.01); *H04R 2225/41* (2013.01)

(58) Field of Classification Search
CPC ... G10L 25/84; H04R 2225/41; H04R 25/407; H04R 25/50; H04R 25/507
USPC ........................................................ 381/312
See application file for complete search history.

(56) References Cited

U.S. PATENT DOCUMENTS

| | | | | |
|---|---|---|---|---|
| 11,363,390 | B2* | 6/2022 | Santos | H04R 25/50 |
| 11,812,223 | B2* | 11/2023 | Santos | G10L 25/30 |
| 2016/0055420 | A1 | 2/2016 | Karanam et al. | |
| 2017/0061978 | A1 | 3/2017 | Wang et al. | |
| 2017/0123824 | A1* | 5/2017 | Franck | G06F 9/453 |

OTHER PUBLICATIONS

Emiya et al., "Subjective and objective quality assessment of audio source separation," IEEE Transactions on Audio, Speech, and Language Processing, vol. 19, pp. 2046-2057, 2011.

International Search Report and Written Opinion dated Feb. 18, 2019 from PCT Application No. PCT/US2018/057713, 11 pages.

Kingma et al., "Adam: A method for stochastic optimization," arXiv preprint arXiv:1412.6980, 2014.

Koizumi et al., "Dnn-based source enhancement self-optimized by reinforcement learning using sound quality measurements", IEEE International Conference on Acoustics, Speech and Signal Processing, 2017, pp. 81-85.

Li et al., "An overview of noise-robust automatic speech recognition", IEEE/ACM Transactions on Audio, Speech, and Language Processing, vol. 22, 2014, pp. 745-777.

Ming et al., "Robust speaker recognition in noisy conditions," IEEE Transactions on Audio, Speech, and Language Processing, vol. 15, pp. 1711-1723, 2007.

Rix et al., "Perceptual evaluation of speech quality (PESQ)—a new method for speech quality assessment of telephone networks and codecs," in IEEE International Conference on Acoustics, Speech, and Signal Processing, 2001, vol. 2, pp. 749-752.

Rothauser et al., "IEEE recommended practice for speech quality measurements", IEEE Transactions on Audio Electroacoust, vol. 17, 1969, pp. 225-246.

Srivastava et al., "Dropout: a simple way to prevent neural networks from overfitting.," Journal of Machine Learning Research, vol. 15, pp. 1929-1958, 2014.

Taal et al., "An algorithm for intelligibility prediction of time-frequency weighted noisy speech," IEEE Transactions on Audio, Speech, and Language Processing, vol. 19, pp. 2125-2136, 2011.

Varga et al., "Assessment for automatic speech recognition: Ii noisex-92: A database and an experiment to study the effect of additive noise on speech recognition systems", Speech Communication, vol. 12, 1993, pp. 247-251.

Vincent et al., "Performance measurement in blind audio source separation," IEEE transactions on audio, speech, and language processing, vol. 14, pp. 1462-1469, 2006.

Wang et al., "A deep neural network for time-domain signal reconstruction", IEEE International Conference on Acoustics, Speech and Signal Processing, 2015, pp. 4390-4394.

Wang et al., "On training targets for supervised speech separation", IEEE/ACM Transactions on Audio, Speech, and Language Processing, vol. 22, 2014, pp. 1849-1858.

Weninger et al., "Discriminatively trained recurrent neural networks for singlechannel speech separation," in IEEE Global Conference on Signal and Information Processing (GlobalSIP), pp. 577-581, 2014.

Williamson et al., "Complex ratio masking for monaural speech separation," IEEE/ACM transactions on audio, speech, and language processing, vol. 24, pp. 483-492, 2016.

Xu et al., "A regression approach to speech enhancement based on deep neural networks," IEEE/ACM Transactions on Audio, Speech, and Language Processing, vol. 23, pp. 7-19, 2015.

Zhao et al., "A two-stage algorithm for noisy and reverberant speech enhancement," in IEEE International Conference on Acoustics, Speech and Signal Processing (ICASSP), pp. 5580-5584, 2017.

* cited by examiner

ELECTRONIC DEVICE USING A COMPOUND METRIC FOR SOUND ENHANCEMENT

RELATED PATENT DOCUMENTS

This application is a continuation of U.S. patent application Ser. No. 17/834,288, filed Jun. 7, 2022, which is a continuation of U.S. patent application Ser. No. 17/074,144, filed Oct. 19, 2020, now U.S. Pat. No. 11,363,390, and which is a continuation of Ser. No. 16/170,858, filed Oct. 25, 2018, now U.S. Pat. No. 10,812,915, which claims the benefit of Provisional Patent Application Ser. No. 62/577,903 filed on Oct. 27, 2017, to which priority is claimed pursuant to 35 U.S.C. § 119(e), and which are incorporated herein by reference in their entireties.

TECHNICAL FIELD

This application relates generally to ear-worn electronic devices, including hearing devices, hearing aids, personal amplification devices, and other hearables.

BACKGROUND

In real-world environments, sound is inevitably corrupted by background noise coming from various sound sources like other speakers, machines and other sources. These distortions degrade speech or other desirable sound intelligibility and quality, especially when the signal-to-noise ratio (SNR) and/or signal-to-interference ratio is low. For both normal hearing (NH) and hearing impaired (HI) listeners, understanding noisy speech usually becomes very challenging.

SUMMARY

Embodiments of the disclosure are directed to a method comprising receiving at least one sound at an electronic device. The at least one sound is enhanced for the at least one user based on a compound metric. The compound metric is calculated using at least two sound metrics selected from an engineering metric, a perceptual metric, and a physiological metric. The engineering metric comprises a difference between an output signal and a desired signal. At least one of the perceptual metric and the physiological metric is based at least in part on input sensed from the at least one user in response to the received at least one sound.

Embodiments are directed to a system comprising an electronic device configured to receive at least one sound. At least one sensor is communicatively coupled to the electronic device. The at least one sensor is configured to sense an input from at least one user of the electronic device in response to the received at least one sound. A processor is communicatively coupled to the electronic device and is configured to enhance the at least one sound for the at least one user based on a compound metric. The compound metric is calculated using at least two sound metrics selected from an engineering metric, a perceptual metric, and a physiological metric. The engineering metric comprises a difference between an output signal and a desired signal.

The above summary is not intended to describe each disclosed embodiment or every implementation of the present disclosure. The figures and the detailed description below more particularly exemplify illustrative embodiments.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
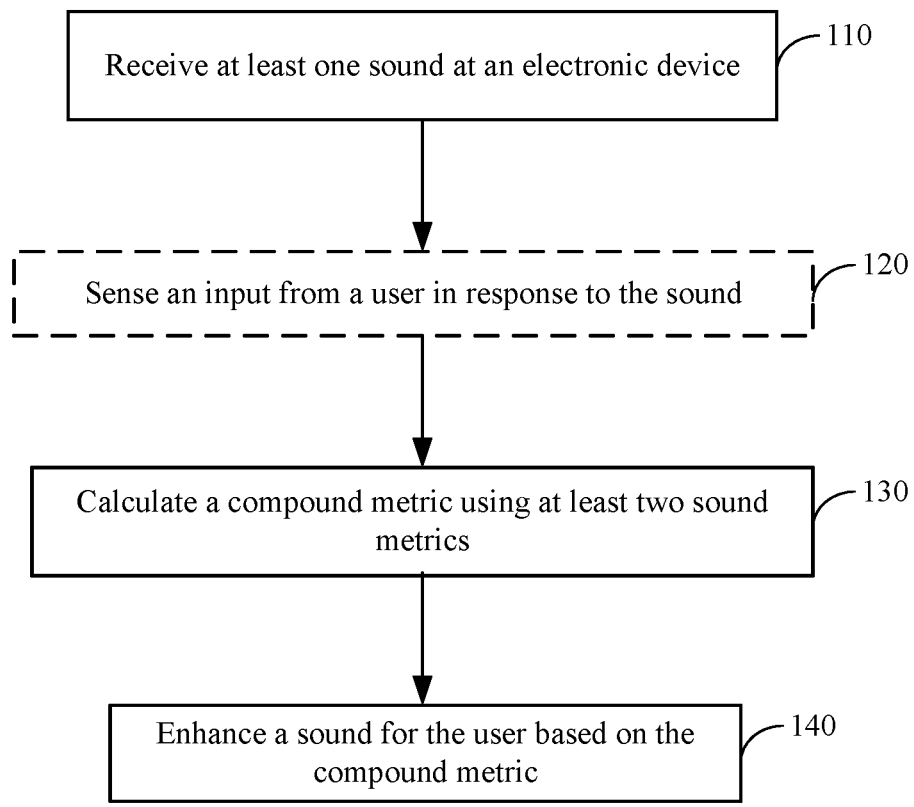
FIGS. 1A and 1B illustrate processes for enhancing a sound for a user in accordance with embodiments described herein.

It is understood that the embodiments described herein may be used with any electronic device configured to enhance an audio signal for a user without departing from the scope of this disclosure. The devices depicted in the figures are intended to demonstrate the subject matter, but not in a limited, exhaustive, or exclusive sense According to various configurations, embodiments described herein may be used with an ear-worn electronic device. The term ear-worn electronic device of the present disclosure refers to a wide variety of ear-level electronic devices that can aid a person with impaired hearing. The term ear-worn electronic device also refers to a wide variety of devices that can produce optimized or processed sound for persons with normal hearing. Ear-worn electronic devices of the present disclosure include hearables (e.g., wearable earphones, headphones, in-ear monitors, earbuds, virtual reality headsets), hearing aids (e.g., hearing instruments), cochlear implants, and bone-conduction devices, for example. Ear-worn electronic devices include, but are not limited to, behind-the-ear (BTE), in-the-ear (ITE), in-the-canal (ITC), invisible-in-canal (IIC), receiver-in-canal (RIC), receiver-in-the-ear (RITE) or completely-in-the-canal (CIC) type hearing devices or some combination of the above. Throughout this disclosure, reference is made to an "ear-worn electronic device," which is understood to refer to a system comprising a left ear device, a right ear device, or a combination of a left ear device and a right ear device. While some embodiments are described as being used with ear-worn electronic devices, it is to be understood that embodiments disclosed herein can be used with any device that takes audio signals as input and outputs enhanced audio signals. For example, embodiments described herein may be used with mobile communication devices and/or television conference systems. In some cases, some configurations involve software running on a computer.

Human listeners often have difficulties understanding speech in the presence of background noise in the real world. Recently, supervised learning based speech enhancement approaches have achieved substantial success, and show significant improvements over the conventional approaches.

However, existing supervised learning based approaches often try to minimize the mean squared error between the enhanced output and the pre-defined training target (e.g., the log power spectrum of clean speech), even though the purpose of such speech enhancement is to improve speech understanding in noise. According to various embodiments, deep neural networks may be use to enhance at least one sound by incorporating an auditory perception model to achieve enhanced sound. Optimizing the proposed perceptually guided cost function is expected to improve speech intelligibility and/or sound quality further. Systematic evaluations show that using the machine learning techniques described herein provides for improved speech intelligibility and/or sound quality for a wide range of signal-to-noise ratios and noise types while maintaining sound quality.

In real-world environments, sound is inevitably corrupted by background noise coming from various sound sources like other speakers, machines and so forth. These distortions degrade both speech intelligibility and quality, especially when the signal-to-noise ratio is low. For both normal hearing and hearing impaired listeners, understanding noisy speech and/or other types of sounds usually becomes very challenging. This is detrimental to effective communication among people. Many speech-related applications, including automatic speech recognition (ASR) and speaker identification (SID), perform poorly under adverse noisy conditions. According to various configurations, various types of noises besides speech can be corrupted by background noises. These other types of noises may include alarms and music, for example.

FIG. 1A illustrates a process for training and enhancing a sound for at least one user in accordance with embodiments described herein. The at least one user may be any subset of users of the electronic device. The subset of users may be determined based on a common characteristic of the users. For example, the subset of users may be determined based on a common age range. The subset of users may include all users of the electronic device. In some cases, the at least one user is only one user of the electronic device.

At least one sound is received 110 at an electronic device. The sound may be one or more of speech, music and an alarm, for example. According to various configurations, the electronic device is an ear-worn electronic device configured to be worn by the at least one user. Optionally, an input from the at least one user of the electronic device is sensed 120 in response to the received at least one sound.

A compound metric using at least two sound metrics is calculated 130, at least one of which may be based on the sensed input. The sound metrics are selected from an engineering metric, a perceptual metric, and a physiological metric. In some cases, one or more of the sound metrics are calculated. In some embodiments, at least one of the sound metrics is a predetermined metric such that the metric has already been calculated and stored in memory. In some cases, the predetermined metric is calculated and/or otherwise determined during a manufacturing process of the electronic device.

According to various configurations, the process of FIG. 1A is implemented during a predetermined testing time period. For example, the process may be implemented during manufacture of the device. In some cases, the process is implemented when a user starts using the device. The process shown in FIG. 1A may be implemented at a plurality of time periods subsequent to the predetermined testing time period. For example, the process may be implemented upon initiation of the device and may be implemented at a subsequent time based on input from the user, for example. In some cases, the process of FIG. 1A is implemented at predetermined times subsequent to manufacture.

According to various configurations, the engineering metric comprises a difference between an output signal and a desired signal. The perceptual metric and the physiological metric are based at least in part on the sensed input. The sound is enhanced 140 based on the compound metric. In some cases, the performance of the system is determined by a mean squared error (MSE) as the engineering metric. The perceptual metric may be calculated based on at least one of a short term objective intelligibility metric (STOI), a hearing-aid speech quality index (HASQI) metric, a hearing-aid speech perception index (HASPI) metric, a perceptual evaluation of speech quality (PESQ) metric, and a perceptual evaluation of audio quality (PEAQ) metric. According to various embodiments, the perceptual metric may be based at least on part by input from the user. One or more sensors may be used to sense at least one physiological signal from the user. For example, a skin conductance signal, a heart rate signal, and/or an eye movement signal may be used to enhance a sound for the at least one user. According to various configurations, at least one electroencephalogram (EEG) sensor may be able to sense one or more of the physiological signals. For example, the EEG sensor may be able to determine eye movement.

Figure 1B:
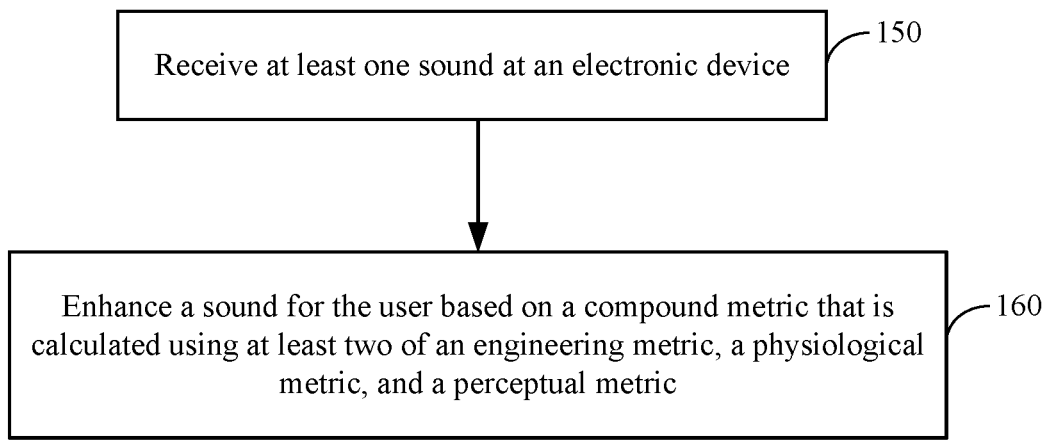

According to various configurations, the process of claim 1A is used for training. In some cases, the compound metric calculated in FIG. 1A is used at a different time to enhance sound for the user. FIG. 1B shows a process for enhancing sound for a user using the compound metric calculated in FIG. 1A. At least one sound is received 150 at an electronic device. The at least one sound is enhanced 160 based on the compound metric calculated in FIG. 1A. As described in conjunction with FIG. 1A, the compound metric is calculated using at least two sound metrics selected from an engineering metric, a perceptual metric, and a physiological metric. In some cases, the compound metric is recalculated at a time other than training to further refine the enhanced sound.

Figure 2:
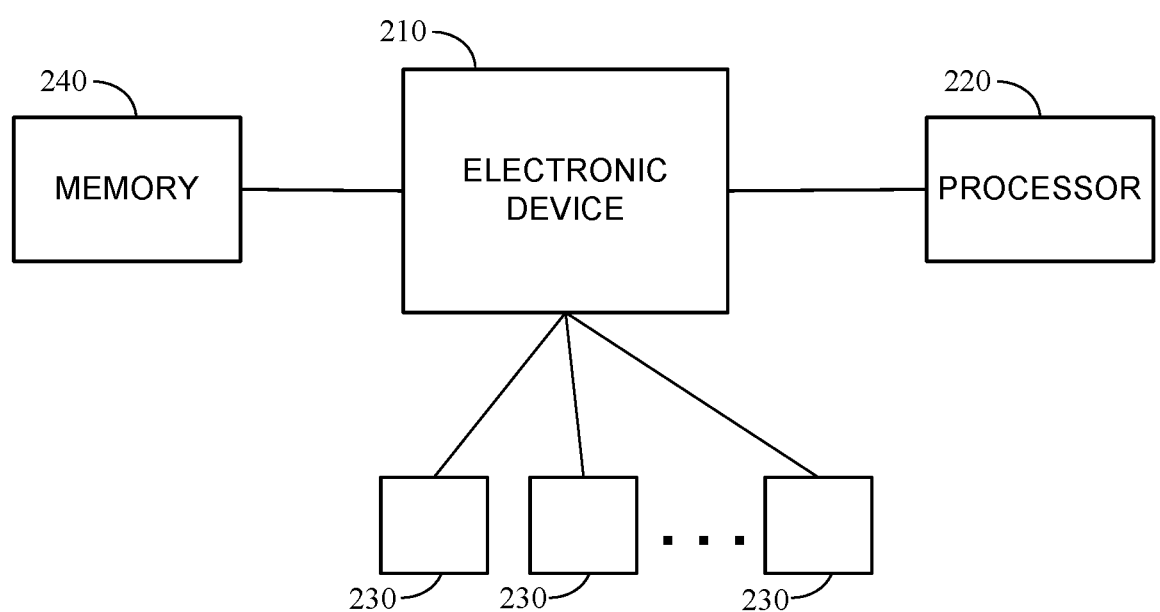
FIG. 2 shows a system for enhancing sound in accordance with various embodiments.

FIG. 2 illustrates a system configured to enhance a sound for the user. An electronic device 210 is configured to receive the sound. The electronic device may be any device that takes audio signals as input and outputs enhanced audio signals. For example, the electronic device may be an ear-worn electronic device configured to be worn by a user. In some cases, the electronic device is a mobile communication device. Optionally, at least one sensor 230 is communicatively coupled to the electronic device 210. The optional sensor 230 is configured to sense an input from a user of the electronic device 210 in response to the received sound.

A processor 220 is communicatively coupled to the electronic device 210. The processor is configured to determine at least two sound metrics selected from an engineering metric, a perceptual metric, and a physiological metric. The processor 220 is configured to calculate a compound metric using the sound metrics and enhance the sound for the user based on the compound metric. The processor 220 may be disposed on the electronic device 210 or in a location different than on the electronic device 210. According to various configurations, the processor is only configured to calculate the compound metric during training of the system. In some cases, the processor is configured to calculate the compound metric during training of the system and at a time subsequent to a training process to further enhance the sound. In some cases, the electronic device 210 is an ear-worn electronic device and the processor is disposed on a mobile communication device. A memory 240 is communicatively coupled to the electronic device 210 and is configured to store the engineering metric, the physiological metric, the perceptual metric, and the compound metric. The memory 240 may store any intermediate calculations needed to calculate any of the metrics and/or any information needed to calculate the above metrics.

According to various implementations, machine learning based approaches may be used to achieve the sound enhancement. For example, neural networks may be used to achieve the sound enhancement. According to various configurations, the system is trained using initial training data during manufacture of the electronic device. In some cases, the system can be trained or re-trained at a time after manufacture. For example, the system may be trained for a particular user or subset of users. A particular training set may be dependent on an age range of a subset of users. In some cases, the system uses feedback from one or more users to train the system. This input can be direct user input in the form of an audible input, a gesture input, and/or a tactile input, for example. The determination of an audible input may be based on one or more sensors communicatively coupled to the electronic device and/or a mobile communication device. The tactile input may be input on a mobile communication device or other device configured to be accessed by the user, for example The determination of the gesture input may be based at least in part on an electroencephalogram (EEG) signal. The EEG signal may be used to detect neural signals indicative of planned, executed, or imagined actions. Additional information about using EEG sensors in an ear-worn electronic device can be found in commonly owned patent U.S. patent application Ser. No. 15/827,856 filed on Nov. 30, 2017 which is incorporated herein by reference in its entirety. According to various configurations, one or more of the sensors may be able to determine the direction that the user is looking, and this determined direction can be used to enhance the sound for the user. In some cases, a user may be looking in a first direction and listening to a sound coming from a different direction. The EEG signals may indicate the direction of the sound that the user is listening to even if it is not the direction that the user is looking.

Figure 3:
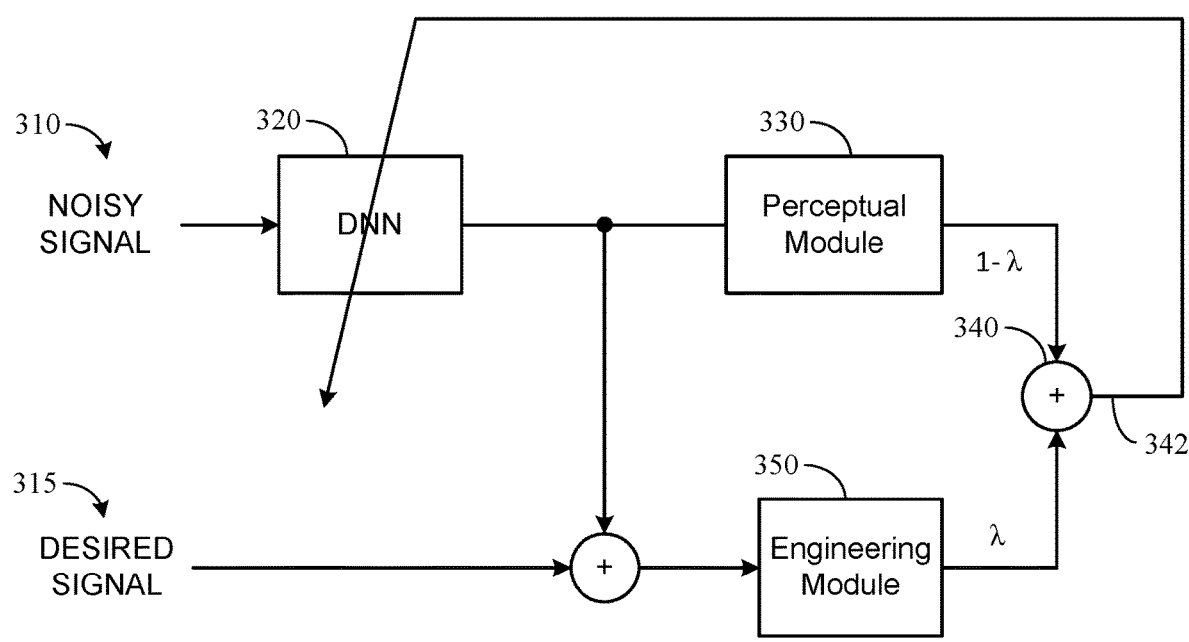
FIG. 3 illustrates an example system for enhancing sound for a user in accordance with various embodiments.

According to various configurations, embodiments described herein use deep learning to achieve enhanced speech. For example, a deep neural network (DNN) may be used. FIG. 3 illustrates an example system for training using two metrics and a DNN to enhance a sound. In this example, an engineering metric and a perceptual metric are used, but it is to be understood that any combination of at least two of an engineering metric, a perceptual metric, and a physiological metric may be used to enhance the at least one sound. FIG. 3 shows an example of training the system to enhance a sound. In this example, a noisy signal 310 and a desired signal 315 are input into the system. An output from the DNN module 320 and the desired signal is input into the engineering module 350 to calculate an engineering metric using an MSE approach, for example. A perceptual module 330 is configured to calculate a perceptual metric using the output from the DNN module 320. A compound metric is calculated 340 using the engineering metric and the perceptual metric. The process shown in FIG. 3 may be iteratively repeated until it is determined that a difference between an output signal and the desired signal 315 is less than a predetermined threshold. λ and λ−1 represent weighting factors that are multiplied with the engineering metric and the perceptual metric, respectively. These weights can be varied to emphasize the engineering metric, the perceptual metric, and/or the physiological metric. After training and calculation of the compound metric, only input of an audio signal 310 and the DNN module 320 may be used to enhance the audio signal.

According to various configurations, the perceptual metric is based on a modified STOI metric. By way of example, the original STOI metric can be calculated in the short-term one-third-octave-band domain with a window length of 384 ms. According to various embodiments, the supervised speech enhancement approach described herein is performed in the short-time Fourier transform (STFT) domain with a 32 ms Hanning window and a 16 ms window shift. Assuming a 16 kHz sampling rate, for each time frame, a 512-point fast Fourier transformation (FFT) is applied, resulting in 257 frequency bins. In order to comply with the STOI calculation, the frequency bins are grouped to form one-third octave bands. Specifically, let $X(m, f)$, $Y(m, f)$ denote the STFT representation of the clean reference signal and the enhanced signal, respectively, at time frame m and frequency channel $f$. Corresponding frequency bins are then combined to 15 one-third octave bands, where the center frequency is set from 150 Hz to around 4.3 kHz. Then, we have the T-F representations as follows in equation (1) below.

$$X_j(m) = \sqrt{\sum_{f=f_1(j)}^{f_2(j)-1} \|X(m, f)\|_2^2} \quad (1)$$

$$Y_j(m) = \sqrt{\sum_{f=f_1(j)}^{f_2(j)-1} \|Y(m, f)\|_2^2}$$

In this example, j is the index of the one-third octave band, $f_1$ and $f_2$ are the edges of the one-third octave bands, and $\|\cdot\|_2$ represents the $L_2$ norm. The short-term temporal envelope of the clean speech and the enhanced speech can be denoted by the following two vectors shown in equation (2).

$$x_{m,j} = [X_j(m), X_j(m+1), \ldots, X_j(m+N-1)]^T$$

$$y_{m,j} = [Y_j(m), Y_j(m+1), \ldots, Y_j(m+N-1)]^T \quad (2)$$

In this example, N is set to 24 corresponding to the 384 ms analysis window length. According to the original STOI computation, the short-term temporal envelope of the enhanced speech is normalized and clipped by using equation (3) below.

$$y_{m,j}(i) = \min\left(\frac{\|x_{m,j}\|_2}{\|y_{m,j}\|_2} y_{m,j}(i), \left(1 + 10^{-\beta/20}\right) x_{m,j}(i)\right) \quad (3)$$

In this example, $i=1, 2, \ldots, N$; $\beta$ controls the lower bound of the signal-to-distortion ratio (SDR). In some cases, $\beta$ is set to $-15$.

The correlation coefficient between the vectors $x_{m,j}$ and $y_{m,j}$ is defined as the intermediate speech intelligibility measure shown in equation (4).

$$d_{m,j} = \frac{\left(x_{m,j} - \mu_{x_{m,j}}\right)^T \left(y_{m,j} - \mu_{y_{m,j}}\right)}{\|x_{m,j} - \mu_{x_{m,j}}\|_2 \|y_{m,j} - \mu_{y_{m,j}}\|_2} \quad (4)$$

In this example, $\mu_{(\cdot)}$ denotes the sample mean of the vector.

The speech intelligibility at time frame m can be calculated by taking average over all one-third octave bands. A modified STOI function at time frame m is shown in equation (5) below.

$$d_m = f(X_m^{24}, Y_m^{24}) = 1/J\Sigma_j d_{m,j} \quad (5)$$

$X_m^{24}$ and $Y_m^{24}$ denote the 24-frame magnitude spectrum starting from the time frame m of the clean reference speech and the corresponding enhanced speech, respectively, J denotes the total number of the one-third octave bands. It is noted that the defined modified STOI function $f$ is a derivative function, since each operation described above is differentiable. Therefore, a modified STOI function $f$ based loss can be optimized by using a backpropagation (BP) algorithm.

A neural network architecture using the modified STOI function can be used and incorporated into a speech enhancement system. According to various implementations, the modified STOI function is used along with an engineering and/or physiological metric to enhance sound. For example, the STOI metric may be used with an engineering metric calculated using the MSE approach.

Figure 4:
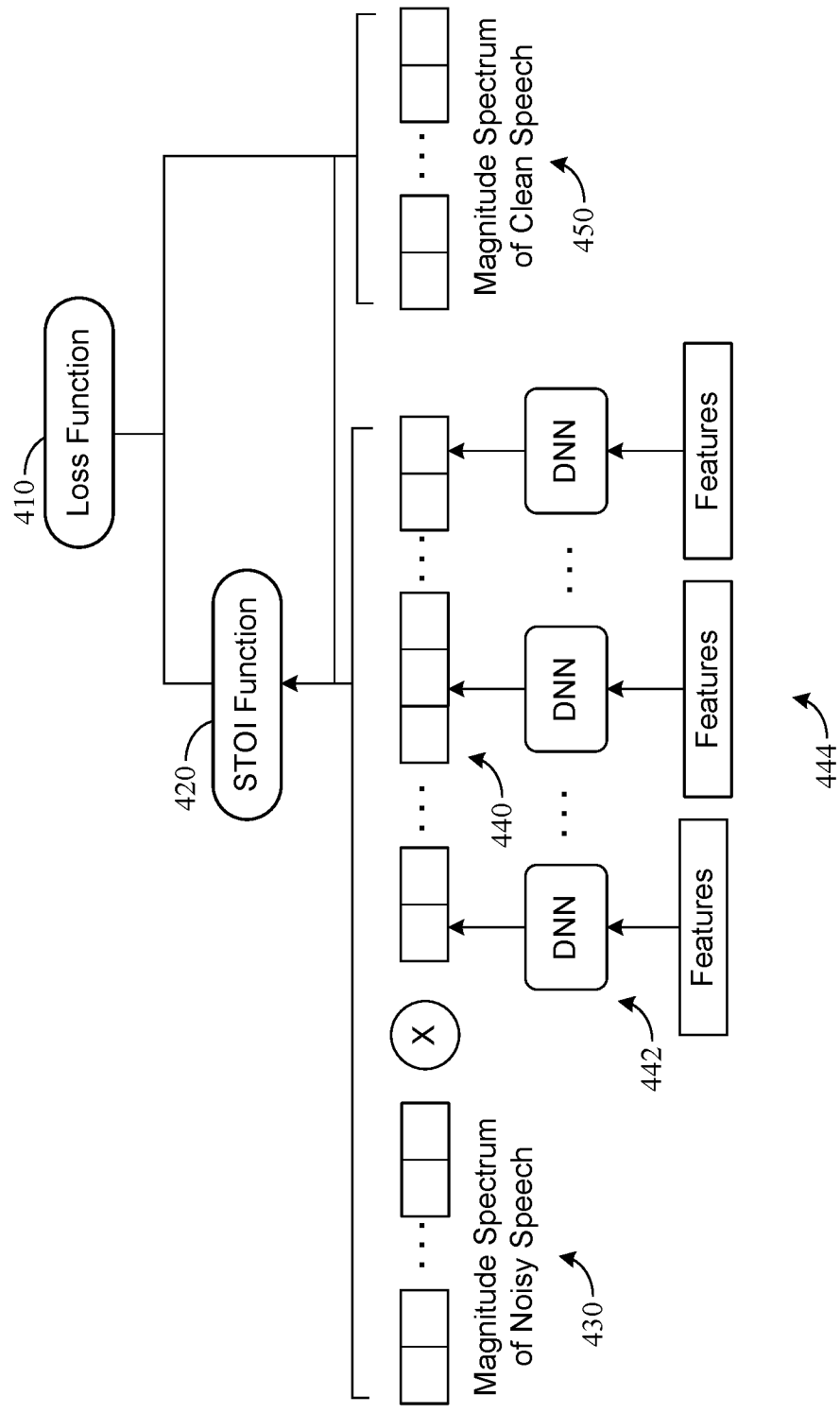
FIG. 4 shows a more detailed system for enhancing sound for a user according to various embodiments described herein.

FIG. 4 shows a more detailed diagram of the proposed network architecture in accordance with various embodiments. For the noisy speech enhancement, a DNN-based denoising system can be used. Specifically, the log magnitude spectrum of the noisy speech is used as features 444 to estimate the ideal ratio mask (IRM), which is defined in equation (6), and then the estimated ratio mask is applied to the noisy magnitude spectrum to obtain the enhanced magnitude spectrum.

$$IRM(m, f) = \sqrt{\frac{X^2(m, f)}{X^2(m, f) + N^2(m, f)}} \quad (6)$$

In this example, $X^2(m, f)$ and $N^2(m, f)$ denote the energy of clean speech and noise, respectively, at time frame m and frequency channel $f$.

A context window may be used to include the features of 2 frames before and 2 frames after the current frame. The ratio mask of the current frame is estimated by using this context information. While FIG. 4 is intended to illustrate 24 DNNs 442, it is to be understood that less than 24 DNNs 442 may be used to implement the sound enhancement. In some cases, only one DNN 442 is used for the sound enhancement. According to various configurations, the 24 DNNs share the same parameters.

By slicing the frames after enhancement, the 24-frame enhanced magnitude spectrum $Y^{24}$ 430 is obtained together with the corresponding 24-frame clean magnitude spectrum $X^{24}$ 450. The modified STOI value 420 can be computed. Then, at time frame m, the loss function 410 is designed as follows in equation (7).

$$\mathcal{L}(m) = (1 - f(X_m^{24}, Y_m^{24}))^2 + \lambda * \|X_m^{24} - Y_m^{24}\|_F / 24 \quad (7)$$

In this example, function $f$ is the previous defined STOI function, $\|\cdot\|_F$ denotes the Frobenius norm, and $\lambda$ denotes a tunable hyper-parameter used to balance the two terms in the loss function. Dividing the second term by 24 serves to average the error in frame level for convenience. This can be merged to $\lambda$. According to various configurations, $\lambda$ is set to 0.01. During training, a pre-trained denoising system is used to initialize the denoising module in the proposed system, and then the whole system is optimized by minimizing the proposed loss. During testing, the enhanced speech is synthesized by using the enhanced magnitude spectrum with the noisy phase spectrum. According to various configurations, the loss function 410 and the modified STOI function 420 are only used during training of the system and are not used to enhance a sound after the training process. In some cases, the loss function 410 and the modified STOI function 420 are used both during training and for enhancing a sound after the initial training process.

Figure 5:
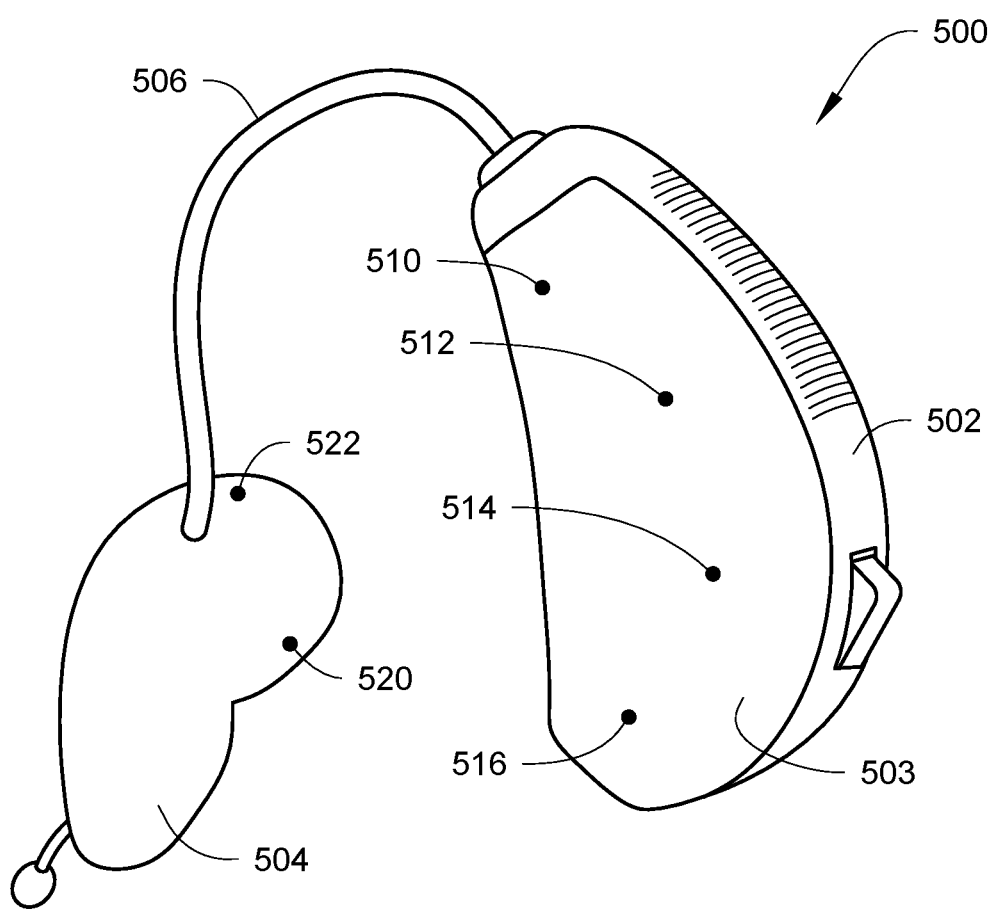
FIG. 5 shows an ear-worn electronic device in accordance with various embodiments.

FIG. 5 shows an ear-worn electronic device 500 which is configured to incorporate any of the embodiments described herein. The device 500 represents one of many different ear-worn electronic devices that can incorporate the disclosed embodiments for enhancing sound for a user. The ear-worn electronic device 500 includes an on-the-ear or behind-the-ear component 502 and a receiver 504 adapted to fit near or in the ear canal of the wearer. The receiver 504 is connected to the component 502 via a tube 506. The component 502 typically includes signal processing electronics, a power source, a microphone (e.g., a microphone array), and a wireless transceiver (e.g., a Bluetooth® transceiver). A number of sensors (e.g., electrodes) 510, 512, 514 and 516 are distributed on the outer surface of the component's housing 503, and are configured to make contact with the wearer's scalp at or proximate to the wearer's ear. The receiver 504 may also include one or more sensors 520, 522. The sensors 520 and 522 situated on the outer surface of the receiver 504 provide for the detection of EEG signals and/or other physiological signals from within the wearer's ear.

Figure 6:
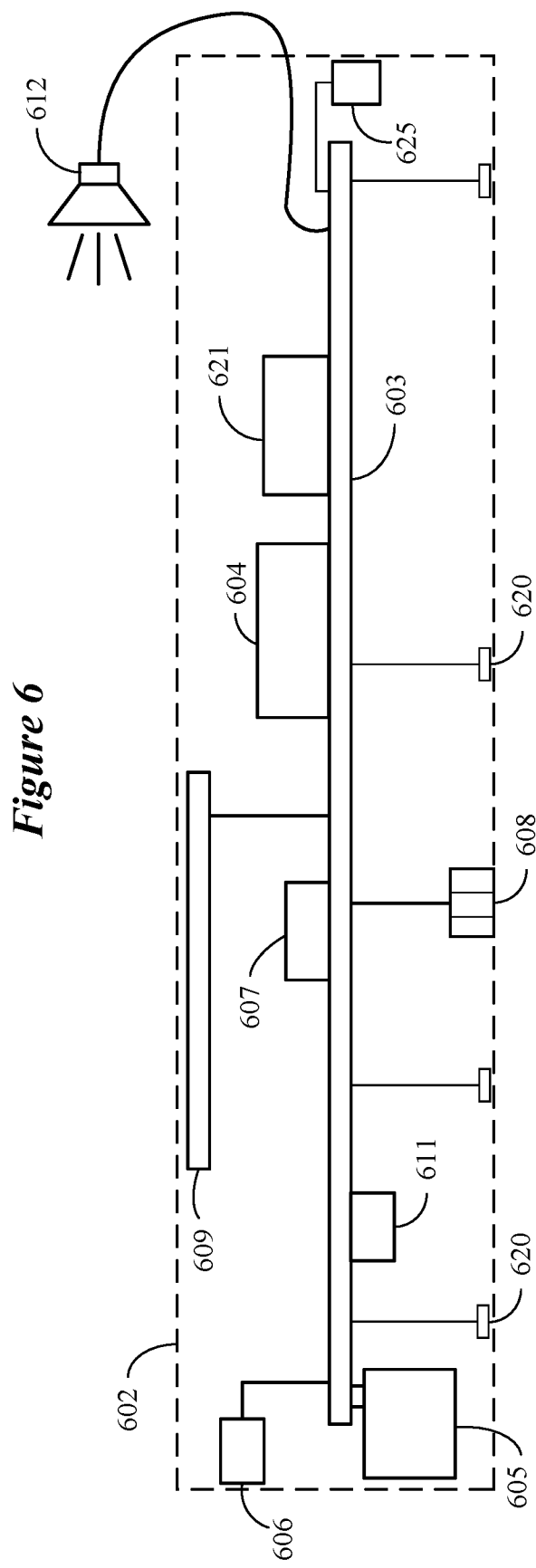
FIG. 6 is a block diagram showing various components that can be incorporated in a system including an ear-worn electronic device in accordance with various embodiments.

FIG. 6 is a block diagram showing various components that can be incorporated in an ear-worn electronic device in accordance with various embodiments. The block diagram of FIG. 6 represents a generic ear-worn electronic device that utilizes the embodiments described herein. Some of the components shown in FIG. 6 can be excluded and additional components can be included depending on the design of the ear-worn electronic device.

The ear-worn electronic device 602 includes several components electrically connected to a mother flexible circuit 603. A battery 605 is electrically connected to the mother flexible circuit 603 and provides power to the various components of the ear-worn electronic device 602. Power management circuitry 611 is coupled to the mother flexible circuit 603. One or more microphones 606 (e.g., a microphone array) are electrically connected to the mother flexible circuit 603, which provides electrical communication between the microphones 606 and a digital signal processor (DSP) 604. Among other components, the DSP 604 incorporates, or is coupled to, audio signal processing circuitry. In some embodiments, the DSP 604 has an audio output stage coupled to a speaker 625. In other embodiments, the DSP 604 has an audio output stage coupled to a receiver 612. The receiver 612 (e.g., a speaker) transforms the electrical signal into an acoustic signal. A physiological data acquisition unit 621 (comprising electronics for physiological data measurement, such as amplifiers and analog-digital conversion) is coupled to one or more physiologic sensors 620 and to the DSP 1104 via the mother flexible circuit 603. One or more user switches 608 (e.g., on/off, volume, mic directional settings) are electrically coupled to the DSP 604 via the flexible mother circuit 603.

The ear-worn electronic device 602 may incorporate a communication device 607 coupled to the flexible mother circuit 603 and to an antenna 609 via the flexible mother circuit 603. The communication device 607 can be a Bluetooth® transceiver, such as a BLE (Bluetooth® low energy) transceiver or other transceiver (e.g., an IEEE 802.11 compliant device). The communication device 607 can be configured to communicate with one or more external devices 650 (which includes one or more processor, e.g., processor 652), such as a smartphone, tablet, laptop, TV, or streaming device. In some embodiments, the communication device 607 provides for direct interaction with cloud computing and storage resources (which includes one or more processor) via telecommunications protocols (e.g., 5G or WiFi).

As was discussed previously, some or all of the processes described hereinabove can be implemented by the DSP 604, alone or in combination with other electronics. The ear-worn electronic device 602 can include dedicated analog and/or digital circuitry configured to support analyses in the time-frequency and spatial domains. In some embodiments, the DSP 604 or other circuitry can be configured to transmit data to an external device (e.g., a smartphone or the cloud) for further processing in the time-frequency and spatial domains. According to some embodiments, communication device 607 can be configured to facilitate communication with another ear-worn electronic device 602 worn by the wearer (e.g., facilitating ear-to-ear communication between left and right devices 602). Features related to the signals acquired at each ear can be communicated between the two ear-worn electronic devices 602.

As described above, the electronic device described herein may be any device that consumes audio signals as input and outputs enhanced audio signals. For example, the electronic device may include a smart phone and/or other portable devices that includes a microphone and a processor.

For convenience, various embodiments for enhancing sound for a user are described herein as being implemented by a processor (e.g., processor 220, DSP 604), which can be representative of any combination of one or more logic devices (e.g., multi-core processors), filters, memory (Flash, RAM, ROM etc.), other digital logic circuitry (e.g., ASICs, FPGAs), analog computing circuits, and software configured to enhance sound for a user in a manner described herein.

In general, the sound enhancement techniques described herein may be implemented in hardware, software, firmware, or any combination thereof. Various features described or illustrated as modules, units or components may be implemented together in an integrated logic device or separately as discrete but interoperable logic devices or other hardware devices. In some cases, various features of electronic circuitry may be implemented as one or more integrated circuit devices, such as an integrated circuit chip or chipset.

If implemented in hardware, embodiments of this disclosure may be directed to an apparatus such a processor or an integrated circuit device, such as an integrated circuit chip or chipset. Alternatively or additionally, if implemented in software or firmware, the techniques disclosed herein may be realized at least in part by a computer-readable data storage medium (e.g., ROM, RAM, SDRAM, NVRAM, EEPROM, FLASH) comprising instructions that, when executed, cause a processor to perform one or more of the methods described herein. For example, the computer-readable data storage medium may store such instructions for execution by a processor.

The code or instructions may be software and/or firmware executed by processing circuitry including one or more processors, such as one or more DSPs, general purpose microprocessors, ASICs, FPGAs, ASSPs, or other equivalent integrated or discrete logic circuitry. Accordingly, the term "processor," as used herein may refer to any of the foregoing structures or any other structure suitable for implementation of the techniques described herein. In addition, in some aspects, functionality described in this disclosure may be provided within software modules or hardware modules. These and other aspects are within the scope of the claims appended hereto.

Example

This example approach was evaluated using the IEEE corpus spoken by a female speaker (see E. H. Rothauser, W. D. Chapman, N. Guttman, K. S. Nordby, H. R. Silbiger, G. E. Urbanek, and M. Weinstock, "IEEE recommended practice for speech quality measurements," IEEE Transactions on Audio Electroacoust, vol. 17, pp. 225-246, 1969), which consists 72 lists with 10 sentences in each list. List 1-50, List 67-72 and List 51-60 were used to construct training data, validation data and test data, respectively. Speech-shaped noise (SSN) and three types of non-stationary noise including speech babble (Babble), factory floor noise (Factory) and destroyer engine room noise (Engine) were used to generate noisy speech in this example study. Each noise segment was 4 min long. The first 3 min was used for training and validation and the remaining was used for testing. For training/validation set, each clean sentence was mixed with 10 random noise segments at three SNR levels, namely, −5, 0 and 5 dB; for the test set, each clean sentence was mixed with 1 random noise segment at five SNR levels, namely, −5, −3, 0, 3 and 5 dB, where −3 and 3 dB SNR conditions were unseen in the training set. Therefore, there were 500×4 (noise types)×3 (SNRs)×10 (noise segments) =60 k utterances in the training set; 50×4 (noise types)×3 (SNRs)×10 (noise segments)=6 k utterances in the validation set; 100×4 (noise types)×5 (SNRs)×1 (noise segment) =2 k utterances in the test set. Neither the sentences nor the noises in the test set were seen during training.

The example system was first compared with a DNN-based masking denoising approach (masking), which employed a DNN to predict the IRM and utilized the estimated ratio mask to perform denoising. It was also used as the denoising module in the example approach. Since part of the designed loss function is similar to that defined in the signal approximation approach (SA), the example approach was compared with the SA approach. The pre-trained masking model was utilized to initialize the SA model. To show that the proposed approach can be considered as a framework to improve the existing supervised speech enhancement approaches, the denoising module was replaced with a DNN-based mapping approach (mapping), which was trained to learn a mapping function from log magnitude spectrum of noisy speech to that of clean speech. This approach was denoted as "mapping+proposed loss". The normal mapping denoising approach was considered as a baseline to compare.

All DNNs in the example study had three hidden layers with 1024 exponential linear units (ELUs) in each layer. These were trained by using Adam optimizer with dropout regularization. The dropout rate in the experiments was set to 0.3. Sigmoid activation units were employed in the output layer for the ratio mask estimation whose value was bounded between 0 and 1; otherwise, linear activation units were used. The input features were normalized to zero mean and unit variance. For the mapping approach, the training target was also normalized by using mean variance normalization.

In this example, STOI, PESQ, and SDR were used to evaluate the speech intelligibility and quality, respectively. Tables 1-3 show the average performance of the three metrics under the four types of noise over the five test SNR levels. The results were averaged over −5, −3, 0, 3, and 5 dB mixtures. Compared with the evaluation scores of noisy speech, each approach improved the STOI, PESQ and SDR performance significantly. Since the objective was to improve the speech intelligibility, the STOI scores of the different systems were compared. As expected, the proposed system achieved the best STOI scores under each noise type. The trends of the performance of different systems were similar under the four types of noise. Taking the Babble noise for an example, the example system improved the masking system by about 2% absolute value. The average scores are shown in Tables 1-3 below. More STOI improvements are observed at lower SNR levels, where the speech intelligibility improvements become more important since the communications are more challenging for human in a very noisy environment. The SA method can also improve the STOI values over the masking method, but the performance is still worse than the example system. By simply replacing the denoising module in our system with the mapping method, more than 2% absolute STOI score improvements were observed under each kind of noise. This indicates that many supervised speech enhancement system can be deployed in our framework and effectively improve the speech intelligibility further.

TABLE 1

| | STOI (in %) | | | |
|---|---|---|---|---|
| System | SNN | Babble | Factory | Engine |
| unprocessed | 71.27 | 68.65 | 68.01 | 73.19 |
| mapping | 81.30 | 77.75 | 79.74 | 86.40 |
| masking | 84.32 | 80.29 | 82.66 | 89.38 |
| SA | 85.01 | 81.17 | 83.18 | 89.23 |
| mapping + proposed loss | 83.39 | 79.94 | 81.82 | 88.14 |
| proposed system | 86.01 | 82.27 | 84.58 | 90.41 |

TABLE 2

| | PESQ | | | |
|---|---|---|---|---|
| System | SNN | Babble | Factory | Engine |
| unprocessed | 1.176 | 1.279 | 1.085 | 1.245 |
| mapping | 2.070 | 1.868 | 2.089 | 2.363 |
| masking | 2.142 | 1.891 | 2.066 | 2.468 |
| SA | 2.242 | 1.992 | 2.198 | 2.564 |
| mapping + proposed loss | 2.034 | 1.855 | 2.011 | 2.329 |
| proposed system | 2.213 | 1.997 | 2.141 | 2.532 |

TABLE 3

| | SDR (dB) | | | |
|---|---|---|---|---|
| System | SNN | Babble | Factory | Engine |
| unprocessed | 0.16 | 0.14 | 0.12 | 0.13 |
| mapping | 5.67 | 5.40 | 7.08 | 8.69 |
| masking | 6.70 | 6.20 | 8.55 | 10.61 |
| SA | 7.46 | 7.01 | 9.17 | 11.30 |
| mapping + proposed loss | 5.50 | 5.19 | 7.07 | 8.80 |
| proposed system | 7.40 | 6.90 | 9.19 | 11.33 |

The improvements in speech intelligibility of the example system were achieved without the expense of a degradation in speech quality. If the two speech quality metrics, PESQ and SDR, are compared, the example system shows comparable performance with the strongest baseline SA system, and outperforms the masking method. In the experiments, it was found that the tunable hyper-parameter A has some influence on the enhanced speech intelligibility and quality. In the example system, a fixed value was used and the value was determined empirically. However, some preliminary experiments using a simple automatically adaptive A show that better results can be obtained under some conditions.

This document discloses numerous embodiments, including but not limited to the following:

Item 1 is a method comprising:
receiving at least one sound at an electronic device; and
enhancing the at least one sound for at least one user based on a compound metric, the compound metric calculated using at least two sound metrics selected from an engineering metric, a perceptual metric, and a physiological metric, the engineering metric comprising a difference between an output signal and a desired signal, at least one of the perceptual metric and the physiological metric based at least in part on input sensed from the at least one user in response to the received at least one sound.

Item 2 is the method of item 1, wherein enhancing the at least one sound for the at least one user comprises enhancing the sound using a neural network to enhance the at least one sound for the at least one user.

Item 3 is the method of item 1, wherein the engineering metric is calculated using a mean squared error (MSE) function of the output signal and the desired signal.

Item 4 is the method of item 1, wherein the perceptual metric is calculated by using at least one of a short term objective intelligibility metric (STOI), a hearing-aid speech quality index (HASQI), a hearing-aid speech perception index (HASPI), a perceptual evaluation of speech quality (PESQ), and a perceptual evaluation of audio quality (PEAQ).

Item 5 is the method of item 1, wherein the compound metric is calculated as a cost function.

Item 6 is the method of item 1, wherein the compound metric is calculated during a predetermined testing time period.

Item 7 is the method of item 6, wherein the compound metric is calculated at a plurality of time periods subsequent to the predetermined testing time period.

Item 8 is the method of item 1, wherein the user input comprises one or more of an audible input, a gesture input, and a tactile input.

Item 9 is the method of item 1, wherein the electronic device is an ear-worn electronic device configured to be worn by the at least one user.

Item 10 is the method of item 1, wherein the electronic device is a mobile communication device.

Item 11 is the method of item 1, wherein the at least one sound comprises one or more of speech, music, and an alarm.

Item 12 is the method of item 1, wherein computing the compound metric comprises building a compound metric model with neural networks using training data.

Item 13 is the method of item 1, further comprising calculating the compound metric in response to the user input.

Item 14 is the method of item 1, further comprising calculating the compound metric in response to the difference between the output signal and the clean signal being greater than a predetermined threshold.

Item 15 is the method of item 1, wherein the physiological metric comprises at least one of an electroencephalogram (EEG) signal, a skin conductance signal, and a heart rate signal.

Item 16 is a system, comprising:
an electronic device configured to receive at least one sound;

at least one sensor communicatively coupled to the electronic device, the at least one sensor configured to sense an input from at least one user of the electronic device in response to the received at least one sound; and a processor communicatively coupled to the electronic device configured to enhance the at least one sound for the at least one user based on a compound metric, the compound metric calculated using at least two sound metrics selected from an engineering metric, a perceptual metric, and a physiological metric, the engineering metric comprising a difference between an output signal and a desired signal.

Item 17 is the system of item 16, wherein the electronic device is an ear-worn electronic device configured to be worn by the at least one user.

Item 18 is the system of item 16, wherein the processor is configured to implement a neural network to enhance the at least one sound for the at least one user.

Item 19 is the system of item 16, wherein the processor is configured to implement at least one of a short term objective intelligibility metric (STOI), a hearing-aid speech quality index (HASQI), a hearing-aid speech perception index (HASPI), a perceptual evaluation of speech quality (PESQ), and a perceptual evaluation of audio quality (PEAQ).

Item 20 is the system of item 16, wherein the at least one sensor comprises one or more of an electroencephalogram (EEG) sensor, a skin conductance sensor, and a heart rate sensor.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. A system, comprising:
   an electronic device configured to receive at least one sound, the electronic device comprising an ear-worn electronic device or a mobile communication device;
   at least one sensor communicatively coupled to the electronic device, the at least one sensor configured to sense an input from at least one user of the electronic device in response to the received at least one sound; and
   a processor communicatively coupled to the electronic device and configured to enhance the at least one sound for the at least one user based on a compound metric using a neural network defining a compound metric model and a loss function.

2. The system of claim 1, wherein the processor is configured to calculate the compound metric using two or more of a perceptual metric, an engineering metric, and a physiological metric.

3. The system of claim 1, wherein the neural network is configured as a denoising system that provides noisy speech enhancement.

4. The system of claim 1, wherein a perceptual metric is incorporated in the loss function.

5. The system of claim 1, wherein a short term objective intelligibility (STOI) metric is incorporated in the loss function.

6. The system of claim 1, wherein the neural network comprises one or more deep neural networks.

7. The system of claim 1, wherein the processor is configured to calculate the compound metric in response to a user input.

8. The system of claim 1, wherein:
the at least one sensor comprises one or more of an electroencephalogram (EEG) sensor configured to produce an EEG signal, a skin conductance sensor configured to produce a skin conductance signal, and a heart rate sensor configured to produce a heart rate signal; and
the processor is configured to calculate a physiological metric of the compound metric using at least one of the EEG signal, the skin conductance signal, and the heart rate signal.

9. The system of claim 1, wherein:
the processor is further configured to train the neural network using training data to build the compound metric model; and
the training data is based on at least one user characteristic.

10. The system of claim 1, wherein:
the processor is further configured to train the neural network based on a user input; and
the user input comprises one or more of an audible input, a gesture input, and a tactile input.

11. The system of claim 1, wherein the processor is configured to calculate the compound metric during a predetermined testing time period.

12. The system of claim 11, wherein the processor is configured to calculate the compound metric at a plurality of time periods subsequent to the predetermined testing time period.

13. The system of claim 1, wherein the at least one sound comprises one or more of speech, music, and an alarm.

14. A method, comprising:
receiving at least one sound at an electronic device, the electronic device comprising an ear-worn electronic device or a mobile communication device;
sensing an input from at least one user of the electronic device in response to the received at least one sound; and
using a neural network defining a compound metric model and a loss function, enhancing the at least one sound for the at least one user based on a compound metric.

15. The method of claim 14, comprising calculating the compound metric using two or more of a perceptual metric, an engineering metric, and a physiological metric.

16. The method of claim 14, wherein a perceptual metric is incorporated in the loss function.

17. The method of claim 14, wherein a short term objective intelligibility (STOI) metric is incorporated in the loss function.

18. The method of claim 14, comprising calculating the compound metric in response to the user input.

19. The method of claim 14, comprising calculating the compound metric using at least one of an EEG signal, a skin conductance signal, and a heart rate signal sensed from the at least one user.

20. The method of claim 14, comprising:
training the neural network using training data to build the compound metric model;
wherein the training data is based on at least one user characteristic.

21. The method of claim 14, comprising:
training the neural network based on a user input;
wherein the user input comprises one or more of an audible input, a gesture input, and a tactile input.

22. The method of claim 14, comprising calculating the compound metric during a predetermined testing time period.

23. The method of claim 22, comprising calculating the compound metric at a plurality of time periods subsequent to the predetermined testing time period.

* * * * *